United States Patent [19] … [11] Patent Number: 4,673,688
Murashige et al. … [45] Date of Patent: Jun. 16, 1987

[54] PARTIAL AMINE SALTS OF EDTA AS BLOOD ANTICOAGULANT

[75] Inventors: Yoshio Murashige, Iwakuni; Akira Yanagase; Yasunori Kawachi, both of Ohtake; Junko Soga, Hiroshima, all of Japan

[73] Assignee: Mitsubishi Rayon Co., Ltd., Tokyo, Japan

[21] Appl. No.: 914,512

[22] Filed: Oct. 2, 1986

Related U.S. Application Data

[63] Continuation of Ser. No. 839,028, Mar. 12, 1986, abandoned, which is a continuation-in-part of Ser. No. 775,358, Sep. 12, 1985, abandoned.

[30] Foreign Application Priority Data

Mar. 28, 1985 [JP] Japan ................................. 60-64612

[51] Int. Cl.$^4$ .................. A61K 31/195; C07C 101/26
[52] U.S. Cl. ................................ 514/554; 260/501.11
[58] Field of Search .......................................... 514/554

[56] References Cited

U.S. PATENT DOCUMENTS

| | | | |
|---|---|---|---|
| 2,700,612 | 1/1955 | Chenicek | 260/501.11 |
| 2,805,203 | 9/1957 | Knapp et al. | 260/501.11 |
| 2,830,019 | 4/1958 | Fields et al. | 260/501.11 |
| 3,534,075 | 10/1970 | Andress | 260/501.11 |
| 3,998,967 | 12/1976 | Weil | 514/554 |

FOREIGN PATENT DOCUMENTS

| | | | |
|---|---|---|---|
| 77406 | 4/1983 | European Pat. Off. | 260/501.11 |
| 817261 | 7/1959 | United Kingdom | 260/501.11 |

*Primary Examiner*—J. E. Evans
*Attorney, Agent, or Firm*—Oblon, Fisher, Spivak, McClelland & Maier

[57] ABSTRACT

There is disclosed a blood anticoagulant consisting essentially of a salt formed by reacting ethylenediaminetetraacetic acid with an alkylenediamine having 2 to 8 carbon atoms in a molar ratio of ethylenediaminetetraacetic acid to alkylenediamine ranging from 1:0.5 to 1:2, or with an alkylamine having 1 to 8 carbon atoms in a molar ratio of ethylenediaminetetraacetic acid to alkylamine ranging from 1:1 to 1:3. This blood anticoagulant is suitable for preventing coagulation of blood collected for purpose of hematological examination.

14 Claims, No Drawings

PARTIAL AMINE SALTS OF EDTA AS BLOOD ANTICOAGULANT

This application is a continuation, of application Ser. No. 839,028, filed Mar. 12, 1986, now abandoned,

BACKGROUND OF THE INVENTION

1. Field of the Invention

This invention relates to blood anticoagulants and, more particularly, to a blood anticoagulant suitable for preventing coagulation of blood collected for purposes of hematological examination.

2. Description of the Prior Art

With the progress of clinical medicine, hematological examination has recently come to play a very important role in the field of preventive medicine or in the judgement of therapeutic effects. Under these circumstances, the development of blood anticoagulants which can prevent coagulation of blood collected for purposes of hematological examination is being actively pursued.

Blood anticoagulants comprising heparin sodium are most widely known. For example, in medical treatments using an artificial kidney or a blood oxygenator, they are added to the blood and/or used for the treatment for equipment surfaces which are in contact with the blood.

Moreover, blood anticoagulants comprising a metallic salt of ethylenediaminetetraacetic acid are being used in certain morphological tests of blood.

These blood anticoagulants are also being used in coating the internal surfaces of hematocrit tubes for the determination of hematocrit which is an item of hematological examination, and as additives for the separation of blood plasma.

However, since heparin is obtained solely by extraction from animal organs, it cannot be produced as abundantly as synthetic products and its production cost is far higher. Moreover, heparin preparations having identical structures and properties are almost impossible to obtain by extraction from different types of organs.

On the other hand, blood anticoagulants comprising a metallic salt of ethylenediaminetetraacetic acid can be used in morphological tests of blood. However, they are disadvantageous in that they do not allow inorganic ion determinations which are among biochemical tests and they exert an adverse effect on enzyme tests. For these reasons, conventional blood tests have unavoidably involved complicated procedures, i.e., the selection of different blood anticoagulants according to the intended test item and the adoption of the serum separation method in which steps must be taken to separate serum from blood prior to measurement.

Accordingly, there is a demand for a blood anticoagulant which is inexpensive, has excellent anticoagulant properties, and exerts no adverse effect on a wide variety of blood tests. However, no blood anticoagulant meeting this demand has been developed as yet.

SUMMARY OF THE INVENTION

It is an object of the present invention to provide a blood anticoagulant which can be used without exerting any adverse effect on various types of blood tests.

It is another object of the present invention to provide a blood anticoagulant which exhibits stable anticoagulant properties and can be produced at low cost.

According to the present invention, there is provided a blood anticoagulant consisting essentially of a salt formed by reacting ethylenediaminetetraacetic acid with an alkylenediamine having 2 to 8 carbon atoms in a molar ratio of ethylenediaminetetraacetic acid to alkylenediamine ranging from 1:0.5 to 1:2.0, or with an alkylamine having 1 to 8 carbon atoms in a molar ratio of ethylenediaminetetraacetic acid to alkylamine ranging from 1:1.0 to 1:3.0.

DETAILED DESCRIPTION OF THE PREFERRED EMBODIMENTS

The ethylenediaminetetraacetic acid (hereinafter abbreviated as EDTA) used in preparing the blood anticoagulant of the present invention should preferably comprise a product having an iron content of 5 ppm or less and an EDTA content of 99.0% by weight or greater.

The alkylenediamine used in preparing the blood anticoagulant of the present invention may be selected from ethylenediamine, propylenediamine, butylenediamine, pentamethylenediamine, hexamethylenediamine, heptamethylenediamine and octamethylenediamine. Methylenediamine cannot be used because it does not exist stably in water.

The alkylamine used in preparing the blood anticoagulant of the present invention may be selected from methylamine, ethylamine, propylamine, n-buthylamine, iso-buthylamine, tert-buthylamine, n-amylamine, secamylamine, tert-amylamine, hexylamine, heptylamine and octylamine.

Alkylenediamines or alkylamines whose alkylene or alkyl group has 9 or more carbon atoms cannot be used because they are almost insoluble in water.

The reaction medium used in preparing the blood anticoagulant of the present invention may suitably comprise water.

EDTA should be reacted with the alkylenediamine in a molar ratio of EDTA to alkylenediamine ranging from 1:0.5 to 1:2.0. The preferred range is from 1:0.9 to 1:1.5. If the alkylenediamine is used in an amount less than 0.5 mole per mole of EDTA, unreacted EDTA will remain and exert an adverse effect on anticoagulant properties. On the other hand, if the alkylenediamine is used in an amount of more than 2.0 moles per mole of EDTA, the amount of unreacted alkylenediamine will increase to an unsuitable degree.

The reaction of EDTA with the alkylenediamine, for the most part, takes place in a molar ratio of 1:1. Even if excess alkylenediamine is added, the molar ratio seldom deviates from 1:1. It is also impossible that a polymer having several tens or more repeating units is formed as a result of alternating addition. This reaction proceeds rapidly at a temperature in the range of 20° to 80° C., but the addition reaction of another alkylenediamine molecule with EDTA having one alkylenediamine molecule added thereto can proceed only with difficulty. In practice, this addition reaction does not proceed in the aforesaid temperature range.

EDTA should be reacted with the alkylamine in a molar ratio of EDTA to alkylamine ranging from 1:1 to 1:3.0. If the alkylamine is used in an amount less than 1 mole per mole of EDTA, unreacted EDTA will remain and exert an adverse effect on anticoagulant properties. On the other hand, if the alkylamine is used in an amount of more than 3.0 moles per mole of EDTA, the amount of unreacted alkylamine will increase to an unsuitable degree.

The reaction of EDTA with the alkylenediamine will proceed easily up to a molar ratio of 1:3.0 at a temperature of 20° to 80° C., but the addition reaction of another alkylamine molecule with EDTA having three alkylamine molecules added thereto do not proceed under ordinary temperatures.

Since EDTA is almost insoluble in water and cannot be formed into highly concentrated aqueous solutions, the alkylenediamine or the alkylamine is added to a dispersion of EDTA in water. Then, since the reaction product of EDTA with the alkylenediamine or the alkylamine is highly soluble in water, the amount of EDTA dispersed in water decreases as the reaction proceeds. When the number of moles of alkylenediamine added becomes almost equal to that of EDTA, or the number of moles of alkylamine added becomes almost two folds to that of EDTA, the reaction mixture gives a perfectly homogeneous solution.

When the alkylenediamine or the alkylamine is added to the dispersion of EDTA, neutralization heat is produced due to the neutralization reaction, resulting in a temperature rise of the reaction mixture. This neutralization heat can be removed by cooling the water or the reaction vessel with a cooling jacket. Where water is used as the solvent, the reaction temperature should preferably be maintained in the range of 20° to 80° C. in order to prevent evaporation of the water.

The reason why EDTA is preferably reacted with the alkylenediamine or the alkylamine in an aqueous medium is that the reaction product is soluble in water and, therefore, the reaction procedure can be simplified. Where EDTA is dispersed in water and then reacted with the alkylenediamine or the alkylaine, the concentration of EDTA should be in the range which allows the reaction product to dissolve in the water. In other words, the concentration of EDTA should preferably be in the range of 5 to 60% by weight and more preferably in the range of 10 to 30% by weight. If the concentration of EDTA is less than 5% by weight, it is so low that operating efficiency will be reduced. If the concentration of EDTA is greater than 60% by weight, the reaction product will reach the solubility limit.

Thus, the alkylenediamine or the alkylamine is added to the dispersion of EDTA until the required molar ratio is attained. The resulting reaction-product is generally obtained by removing the water. However, since the resulting reaction product contains such impurities as unreacted alkylenediamine and alkylamine, it is preferable to subject the reaction product to a purification procedure.

One such purification procedure is precipitation with a bad solvent. Useful bad solvents include, for example, alcohols such as methanol, ethanol and isopropanol; ketones such as acetone and methyl ethyl ketone; and water-soluble solvents such as dimethylformamide. Among these bad solvents, methanol and acetone having a purity of 98% by weight or greater are especially useful. Where methanol or acetone is used for this purpose, the reaction product can be purified by adding the resulting aqueous solution of the reaction product to methanol or acetone, separating the precipitate so formed, and then drying it. In order to use the reaction product as a blood anticoagulant, it is preferable to remove any residual solvent resulting from the precipitation process. The reason for this is that, if the blood anticoagulant contains a considerable amount of solvent, it may cause hemolysis. Accordingly, the amount of solvent remaining in the reaction product purified by precipitation with solvent should preferably be 1.0% by weight or less. Such residual solvent can be decreased, for example, by dissolving in water the reaction product purified by precipitation with solvent, and evaporating the solution under reduced pressure to expel water and solvent therefrom.

Although it is preferable to use the blood anticoagulant of the present invention alone, it may contain, for example, heparin salts, salts of oxalic acid, double salts of oxalic acid, or salts of citric acid, as long as they are present in such low quantities as to exert no influence on the results of blood tests.

When the blood anticoagulant of the present invention is used for purposes of hematological examination, it is possible to obtain RBC, WBC and platelet counts and hematocrit values which are virtually equivalent to those obtained with commercially available blood anticoagulants. Moreover, the blood anticoagulant of the present invention makes it possible to determine the sodium, potassium and chloride ion levels in blood which cannot be determined with commercially available blood anticoagulants such as heparin sodium. Further, a combination of sodium fluoride and the blood coagulant of the present invention can be used as a blood anticoagulant for the determination of blood glucose levels.

The present invention is further illustrated by the following examples:

EXAMPLE 1

29.2 g (0.1 mole) of EDTA was dispersed in 200 ml of deionized water. While the dispersion was being stirred at room temperature, 6.6 g (0.11 mole) of ethylenediamine was added dropwise thereto at a rate of 0.1 ml/min. After completion of the addition, the reaction was continued at 60° C. for an hour. Upon cooling, the reaction product was precipitated by the addition of 1 liter of methanol having a purity of 98%. The reaction product was collected by filtration, dissolved in 300 ml of deionized water, and then dehydrated and dried in a rotary evaporator to obtain 34.2 g of a fine powder. This fine powder had a methanol content of 0.10% by weight and a water content of 1.2% by weight.

When 2 mg of the above fine powder was placed in a test tube and 2 ml of fresh human blood was added thereto, it exhibited anticoagulant properties and prevent coagulation of the blood. A sample of the blood was fed to an automatic blood counter to determine the RBC, WBC and platelet counts and hematocrit value. The results are shown in Table 1. It may be seen that the aforesaid fine powder has as excellent an anticoagulant effect on blood as the commercially available blood anticoagulant Anticlot ET (trade mark; manufactured by Clinton Laboratories) whose results are also shown in Table 1 as the Reference Example. Anticlot ET, which is an aqueous solution containing 8% by weight of ethylenediaminetetraacetic acid tetrasodium salt and 1.5% by weight of heparin sodium, was used in an amount of 0.04 ml per 2 ml of blood.

TABLE 1

| Blood anti-coagulant | WBC count ($\times 10^{-3}$/ml) | RBC count ($\times 10^{-4}$/ml) | Platelet count ($\times 10^{-4}$/ml) | Hematocrit (%) |
|---|---|---|---|---|
| Example 1 | 6.7 | 464 | 26 | 45 |
| Reference Example | 6.6 | 462 | 26 | 46 |

EXAMPLES 2 and 3

The procedure of Example 1 was repeated except that, as the alkylenediamine to be reacted with EDTA, 8.14 g (0.11 mole) of propylenediamine (Example 2) or 12.76 g (0.11 mole) of hexamethylenediamine (Example 3) was used in place of 6.6 g of ethylenediamine. The resulting reaction products were purified in the same manner as in Example 1 to obtain fine powders. Both of these fine powders exhibited blood anticoagulant properties, and their amounts required to stabilize 1 ml of fresh human blood without causing coagulation thereof were compared. The results are shown in Table 2. It can be seen that both the reaction product of EDTA with propylenediamine (Example 2) and the reaction product of EDTA with hexamethylenediamine (Example 3) act effectively as blood anticoagulants.

TABLE 2

| Blood anticoagulant | Minimum amount required to prevent coagulation of 1 ml of blood (mg)* |
| --- | --- |
| Example 1 | 1.5 |
| Example 2 | 2.0 |
| Example 3 | 3.0 |

*Varying amounts of each blood anticoagulant were added to 1-ml samples of blood. After gentle mixing, these samples were observed at intervals of 5 minutes. Thus, the minimum amount that did not cause blood coagulation after 15 minutes was determined.

EXAMPLE 4

As a blood anticoagulant, 2 mg of the reaction product obtained in Example 1 was added to 1 ml of blood. Then, the sodium, potassium and chloride ion levels in this blood were measured with a compact electrolyte analyzer. The results are shown in Table 3 where the measured values obtained by the conventional serum separation method are also shown for purposes of comparison.

Thus, when the reaction product obtained in Example 1 is used as a blood anticoagulant, blood samples can be directly measured to determine their ion levels. However, this is impossible with commercially available blood anticoagulants comprising a metallic salt of EDTA.

TABLE 3

|  | Sodium ion (mmoles/liter) | Potassium ion (mmoles/liter) | Chloride ion (mmoles/liter) |
| --- | --- | --- | --- |
| Reaction product of Example 1 | 147 | 4.1 | 109 |
| Serum separation method | 147 | 4.0 | 108 |

EXAMPLES 5 and 6

Experiments were carried out in the same manner as in Example 1, except that the amount of ethylenediamine reacted with 29.2 g (0.1 mole) of EDTA was decreased to 3.3 g (0.055 mole) (Example 5) or increased to 9.6 g (0.16 mole) (Example 6). Thus, there were obtained 30.5 g and 36.0 g, respectively, of powders. These powders had methanol contents of 0.08% by weight and 0.07% by weight, and water contents of 1.0% by weight and 1.3% by weight, respectively. Then, 2 mg of each powder was placed in a test tube and 1.5 ml of fresh human blood was added thereto. In both cases, the powder exhibited anticoagulant properties and prevented coagulation of the blood even after 60 minutes. When a portion of the blood was taken and the morphology of red blood cells, white blood cells and platelets was examined under a microscope, no abnormalities were noted in either case.

COMPARATIVE EXAMPLE 1

19.2 g (0.1 mole) of EDTA was dispersed in 200 ml of deionized water. While the dispersion was being stirred at room temperature, 1.5g (0.025 mole) of ethylenediamine was added dropwise thereto. After completion of the reaction, the reaction mixture was treated in the same manner as in Example 1 to obtain a fine powder. This fine powder had a methanol content of 0.08% by weight and a water content of 0.8% by weight. When 4 mg of the above fine powder was placed in a test tube and about 1 ml of fresh blood was added thereto, the blood coagulated after 15 minutes.

EXAMPLE 7

The procedure of Example 1 was repeated except that 14.6 g (0.2 mole) of n-butylamine was used in place of 66 g (0.1 mole) of ethylenediamine. The resulting product was purified in the same manner as in Example 1 except that acetone having a purity of 99% was used in place of methanol to obtain 42.0 g of a fine powder having an acetone content of 0.10% by weight and a water content of 1.2% by weight.

When 2 mg of the above fine powder was placed in a test tube and 2 ml of fresh human blood was added thereto, it exhibited anticoagulant properties and prevented coagulation of the blood. A sample of the blood was fed to an automatic blood counter in the same manner as in Example 1, and the results are shown in Table 4.

TABLE 4

| Blood anti-coagulant | WBC count ($\times 10^{-3}$/ml) | RBC count ($\times 10^{-4}$/ml) | Platelet count ($\times 10^{-4}$/ml) | Hematocrit (%) |
| --- | --- | --- | --- | --- |
| Example 7 | 8.4 | 514 | 27.4 | 46.8 |
| Reference Example | 8.3 | 510 | 27.3 | 46.8 |

EXAMPLES 8 to 10

The procedure of Example 7 was repeated except that, as the alkylamine to be reacted with EDTA, 11.8 g (0.2 mole) of n-propylamine (Example 8), 17.43 g (0.2 mole) of amylamine (Example 9) or 25.9 g (0.2 mole) of octylamine (Example 10) was used in place of 14.6 g of n-butylamine. The resulting reaction products were purified in the same manner as in Example 7 to obtain fine powders. All of these fine powders exhibited blood anticoagulant properites, and the amounts required to stabilize 1 ml of fresh human blood without causing coagulation thereof were compared in the same manner as in Example 2. The results are shown in Table 5.

TABLE 5

| Blood anticoagulant | Minimum amount required to prevent coagulation of 1 ml of blood (mg) |
| --- | --- |
| Example 7 | 1.5 |
| Example 8 | 1.5 |
| Example 9 | 2.0 |
| Example 10 | 2.5 |

EXAMPLE 11

The procedure of Example 4 was repeated except that 2 mg of the reaction product of Example 7 was used in place of the reaction product of Example 1. The results are shown in Table 6.

TABLE 6

| | Sodium ion (mmoles/liter) | Potassium ion (mmoles/liter) | Chloride-ion (mmoles/liter) |
|---|---|---|---|
| Reaction product of Example 7 | 149 | 3.9 | 106 |
| Serum separation method | 149 | 3.9 | 105 |

EXAMPLES 12 and 13

Experiments were carried out in the same manner as in Example 7, except that the amount of n-butylamine reacted with 29.2 g (0.1 moles) of EDTA was decreased to 8.03 g (0.11 mole) (Example 12) or increased to 21.9 g (0.3 mole) (Example 13). Thus, there were obtained 35.3 g and 45.3 g, respectively, of powders. These powders had acetone contents of 0.08% by weight and 0.07% by weight, and water contents of 1.0% by weight and 1.3% by weight, respectively. Then, 2 mg of each powder was placed in a test tube and 1.5 ml of fresh human blood was added thereto. In either case, the powder exhibited anticoagulant properties and prevented coagulation of the blood even after 60 minutes. When a portion of the blood was taken and the morphology of red blood cells, white blood cells and platelets was examined under a microscope, no abnormalities were noted in either case.

COMPARATIVE EXAMPLE 2

29.2 g (0.1 mole) of EDTA was dispersed in 200 ml of deionized water. While the dispersion was being stirred at room temperature, 3.66 g (0.05 mole) of n-butylamine was added dropwise thereto. After completion of the reaction, the reaction mixture was treated in the same manner as in Example 7 to obtain a fine powder. This fine powder had an acetone content of 0.08% by weight and a water content of 0.8% by weight. When 4 mg of the above fine powder was placed in a test tube and about 1 ml of fresh blood was added thereto, the blood coagulated after 15 minutes

EXAMPLE 14

The procedure of Example 7 was repeated except that 30.0 g of 30% by weight of an ethylamine aqueous solution (0.2 mole) was used in place of 14.6 g (0.2 mole) of n-butylamine. After completion of the reaction, the water, i.e., the reaction medium, was taken off by a vacuum drier. Then the mass of the resulting reaction product was crushed to obtain 37.0 g of a fine powder.

When 2 mg of the above fine powder was placed in a test tube and 2 ml of fresh human blood was added thereto, it exhibited anticoagulant properties and prevented coagulation of the blood. A sample of the blood was fed to an automatic blood counter in the same manner as in Example 1, and the results are shown in Table 7.

TABLE 7

| Blood anti-coagulant | WBC count ($\times 10^{-3}$/ml) | RBC count ($\times 10^{-4}$/ml) | Platelet count ($\times 10^{-4}$/ml) | Hema-tocrit (%) |
|---|---|---|---|---|
| Example 14 | 8.2 | 504 | 27.7 | 46.5 |
| Reference Example | 8.3 | 510 | 27.3 | 46.8 |

EXAMPLE 15

The procedure of Example 7 was repeated except that 30.0 g of 30% by weight of 97 ethylamine aqueous solution (92 mole) was used in place of 14.6 g (0.2 mole) of n-butylamine. The resulting product was purified in the same manner as in Example 7 to obtain 37.4 g of a fine powder having an acetone content of 0.13% by weight and a water content of 0.8% by weight.

When 2 mg of the above fine powder was placed in a test tube and 2 ml of fresh human blood was added thereto, it exhibited anticoagulant properties and prevented coagulation of the blood. A sample of the blood was fed to an automatic blood counter in the same manner as in Example 1, and the results are shown in Table 8.

TABLE 8

| Blood anti-coagulant | WBC count ($\times 10^{-3}$/ml) | RBC count ($\times 10^{-4}$/ml) | Platelet count ($\times 10^{-4}$/ml) | Hema-tocrit (%) |
|---|---|---|---|---|
| Example 15 | 8.3 | 511 | 27.4 | 46.8 |
| Reference Example | 8.3 | 510 | 27.3 | 46.8 |

EXAMPLE 16

The procedure of Example 4 was repeated except that 2 mg of the reaction product of Example 15 was used in place of the reaction product of Example 1. The results are shown in Table 9.

TABLE 9

| | Sodium ion (mmoles/liter) | Potassium ion (mmoles/liter) | Chloride-ion (mmoles/liter) |
|---|---|---|---|
| Reaction product of Example 15 | 149 | 3.9 | 104 |
| Serum separation method | 149 | 3.9 | 105 |

EXAMPLES 17 and 18

Experiments were carried out in the same manner as in Example 15, except that the amount of 30% by weight of an ethylamine aqueous solution reacted with 29.2 g (0.1 moles) of EDTA was decreased to 16.5 g (0.11 mole)(Example 17) or increased to 45.0 g (0.3 mole) (Example 18). Thus, there were obtained 32.9 g and 41.9 g, respectively, of powders. These powders had acetone contents of 0.09% by weight and 0.07% by weight, and water contents of 0.9% by weight and 1.3% by weight, respectively. Then, 2 mg of each powder was placed in a test tube and 1.5 ml of fresh human blood was added thereto. In either case, the powder exhibited anticoagulant properties and prevented coagulation of the blood even after 60 minutes. When a portion of the blood was taken and the morphology of red blood cells, white blood cells and platelets was examined under a microscope, no abnormalities were noted in either case.

What is claimed is:

1. A method for preventing the coagulation of blood, comprising:

contacting blood with an effective amount of an anticoagulant comprising a salt formed by reacting ethylenediaminetetraacetic acid with an alkylenediamine having 2 to 8 carbon atoms in a molar ratio of ethylenediaminetetraacetic acid to ethylenediamine ranging from 1.0:0.5 to 1.0:2.0, or with an alkylamine having 1 to 8 carbon atoms in a molar ratio of ethylenediaminetetracetic acid to alkylamine ranging from 1.0:1.0 to 1.0:3.0.

2. The method of claim 1, wherein said molar ratio of ethylenediaminetetracetic acid to alkylenediamine ranges from 1.0:0.9 to 1.0:1.5.

3. The method of claim 1, wherein said ethylenediaminetetraacetic acid has an iron content of 5 ppm or less.

4. The method of claim 1, wherein said alkylenediamine is selected from the group consisting of ethylenediamine, propylenediamine, butylenediamine, pentamethylenediamine, hexamethylenediamine, heptamethylenediamine and octamethylenediamine.

5. The method of claim 1, wherein said alkylamine is selected from the group consisting of methylamine, ethylamine, propylamine, and butylamine, iso-butylamine, tert-butylamine, n-amylamine, secamylamine, tert-amylamine, hexylamine, heptylamine and octylamine.

6. The method of claim 1, wherein said anticoagulant further comprises a compound selected from the group consisting of heparin salts, salts of oxalic acid, double salts of oxalic acid, and salts of citric acid.

7. The method of claim 1, wherein said anticoagulant further comprises sodium fluoride.

8. A blood anticoagulant composition, comprising:
(a) blood, and
(b) an effective amount of an anticoagulant comprising a salt formed by reacting ethylenediaminetetraacetic acid with an alkylenediamine having 2 to 8 carbon atoms in a molar ratio of ethylenediaminetetraacetic acid to ethylenediamine ranging from 1.0:0.5 to 1.0:2.0, or with an alkylamine having 1 to 8 carbon atoms in a molar ratio of ethylenediaminetetracetic acid to alkylamine ranging from 1.0:1.0 to 1.0:3.0.

9. the composition of claim 8, wherein said molar ratio of ethylenediaminetetraacetic acid to alkylenediamine ranges from 1.0:0.9 to 1.0:1.5.

10. The composition of claim 8, wherein said ethylenediaminetetraacetic acid has an iron content of 5 ppm or less.

11. The composition of claim 8, wherein said alkylenediamine is selected from the group consisting of ethylenediamine, propylenediamine, butylenediamine, pentamethylenediamine, hexamethylenediamine, heptamethylenediamine and octamethylenediamine.

12. The composition of claim 8, wherein said alkylamine is selected from the group consisting of methylamine, ethylamine, propylamine, and butylamine, isobutylamine, tert-butylamine, n-amylamine, secamylamine, tert-amylamine, hexylamine, heptylamine and octylamine.

13. The composition of claim 8, wherein said anticoagulent for the comprises a compound selected from the group consisting of heparin salts, salts of oxalic acid, double salts of oxalic acid and salts of citric acid.

14. The composition of claim 8, wherein said anticoagulent further comprises sodium fluoride.

* * * * *